US011071805B2

(12) United States Patent
Laub et al.

(10) Patent No.: US 11,071,805 B2
(45) Date of Patent: *Jul. 27, 2021

(54) FIBRINOGEN-BASED TISSUE ADHESIVE PATCHES

(71) Applicant: SEALANTIUM MEDICAL LTD., Rosh Ha'Ayin (IL)

(72) Inventors: Orgad Laub, Tel Aviv (IL); Daniel Cohn, Jerusalem (IL); Eran Cohen, Hod HaSharon (IL); Matthew Zarek, Raanana (IL)

(73) Assignee: SEALANTIUM MEDICAL LTD., Rosh Ha'ayin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/041,903

(22) Filed: Jul. 23, 2018

(65) Prior Publication Data
US 2018/0326115 A1 Nov. 15, 2018

Related U.S. Application Data

(63) Continuation-in-part of application No. 14/785,857, filed as application No. PCT/IL2014/050347 on Apr. 10, 2014, now abandoned.
(Continued)

(51) Int. Cl.
A61L 15/16 (2006.01)
A61L 15/32 (2006.01)
(Continued)

(52) U.S. Cl.
CPC ............ A61L 27/225 (2013.01); A61L 15/16 (2013.01); A61L 15/32 (2013.01); A61L 27/18 (2013.01);
(Continued)

(58) Field of Classification Search
None
See application file for complete search history.

(56) References Cited

U.S. PATENT DOCUMENTS 5,631,011 A * 5/1997 Wadstrom ............... A61L 27/34
424/400
6,054,122 A 4/2000 MacPhee et al.
(Continued)

FOREIGN PATENT DOCUMENTS

WO 2006/044882 A2 4/2006
WO 2008/019128 A2 2/2008
WO 2014/174509 A1 10/2014

OTHER PUBLICATIONS

Kobayashi, H., et al. J. Biomed. Mater. Res. (1991), 25; 1481-1494.*
(Continued)

Primary Examiner — Kevin S Orwig
(74) Attorney, Agent, or Firm — The Roy Gross Law Firm, LLC; Roy Gross

(57) ABSTRACT

A novel fibrinogen-based tissue adhesive patch is disclosed. The patch comprises a backing made from a non-permeable biocompatible polymer film into which a fibrinogen-based sealant is incorporated. In preferred embodiments of the invention, the biocompatible polymer film comprises units of a biocompatible block copolymer such as a polyethylene glycol-polycaprolactone-DL-lactide copolymer connected by urethane linkages, and the fibrinogen-based sealant comprises fibrinogen, thrombin, and $CaCl_2$. In contrast to similar patches known in the art, the polymer backing serves to seal the tissue to which the patch is applied, and the sealant acts only to bind the patch to the affected tissue. The patch does not include any mesh, woven, or non-woven component. Methods of production and use of the patch are also disclosed.

28 Claims, 12 Drawing Sheets

Related U.S. Application Data

(60) Provisional application No. 61/814,355, filed on Apr. 22, 2013.

(51) Int. Cl.
| | |
|---|---|
| *C07K 14/75* | (2006.01) |
| *A61L 27/22* | (2006.01) |
| *A61L 27/60* | (2006.01) |
| *A61L 27/36* | (2006.01) |
| *A61L 27/58* | (2006.01) |
| *C09J 175/04* | (2006.01) |
| *A61L 27/18* | (2006.01) |
| *A61F 2/10* | (2006.01) |

(52) U.S. Cl.
CPC .......... *A61L 27/3683* (2013.01); *A61L 27/58* (2013.01); *A61L 27/60* (2013.01); *C07K 14/75* (2013.01); *C09J 175/04* (2013.01); *A61F 2/105* (2013.01); *A61L 2400/04* (2013.01); *A61L 2430/40* (2013.01)

(56) References Cited

U.S. PATENT DOCUMENTS

| | | | |
|---|---|---|---|
| 6,056,970 A * | 5/2000 | Greenawalt | A61L 15/32 424/422 |
| 6,162,241 A | 12/2000 | Coury et al. | |
| 6,194,005 B1 | 2/2001 | Farah et al. | |
| 6,495,127 B1 | 12/2002 | Wallace | |
| 6,579,537 B2 | 6/2003 | Seelich et al. | |
| 6,699,844 B2 | 3/2004 | Jones et al. | |
| 7,189,410 B1 | 3/2007 | Drohan et al. | |
| 2006/0155235 A1 | 7/2006 | Sawyer | |
| 2007/0059346 A1 | 3/2007 | Maibach | |
| 2011/0071498 A1* | 3/2011 | Hakimimehr | A61L 31/141 604/509 |
| 2011/0250283 A1* | 10/2011 | Mitra | A61K 9/0019 424/497 |
| 2011/0288462 A1 | 11/2011 | Riesinger | |
| 2012/0070485 A1* | 3/2012 | Soldani | A61L 15/32 424/443 |
| 2012/0121532 A1 | 5/2012 | Goessl et al. | |
| 2014/0107159 A1* | 4/2014 | Ebersole | A61L 27/34 514/330 |

OTHER PUBLICATIONS

International Search Report of PCT/IL2014/050347, dated Oct. 30, 2014.
Written Opinion of PCT/IL2014/050347, dated Oct. 22, 2015.
International Preliminary Report of PCT/IL2014/050347, dated Oct. 27, 2015.

* cited by examiner

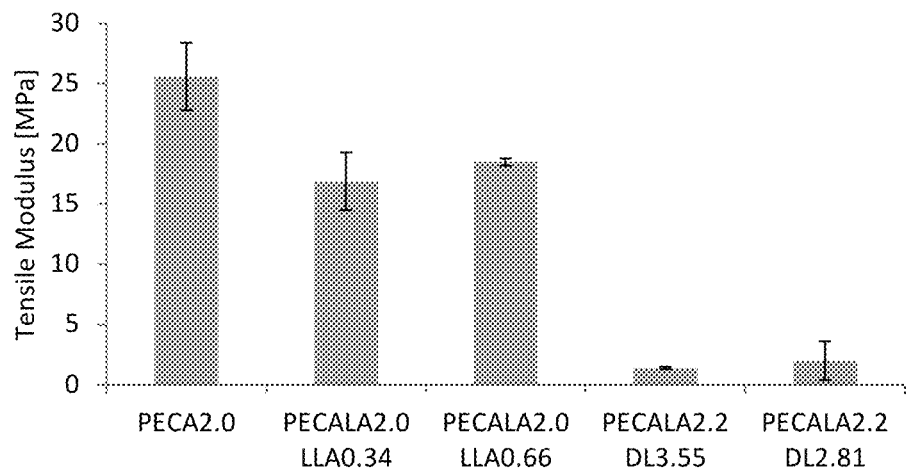
FIG. 4A
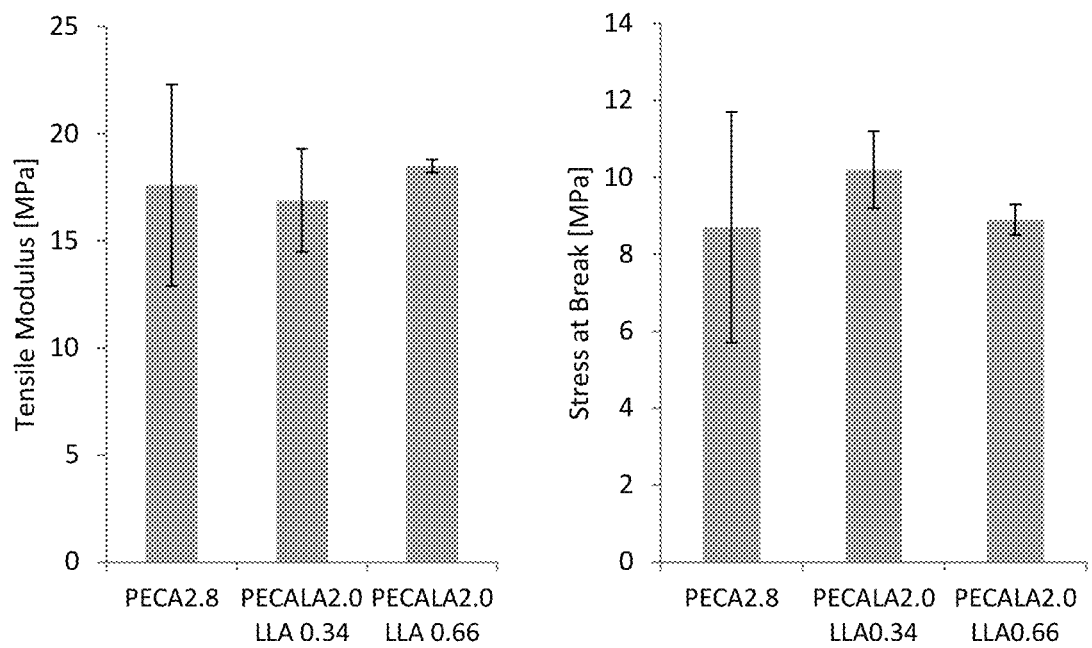
FIG. 4B
FIG. 4C

FIBRINOGEN-BASED TISSUE ADHESIVE PATCHES

REFERENCE TO RELATED PUBLICATIONS

This application is a Continuation-in-Part of U.S. patent application Ser. No. 14/785,857, filed 21 Oct. 2015, which is a national-phase entry of PCT Application No. PCT/IL2014/050347, filed 10 Apr. 2014, which claims priority from U.S. Provisional Application No. 61/814,355, filed 22 Apr. 2013. All of these prior applications are incorporated by reference in their entirety.

FIELD OF THE INVENTION

This invention relates generally to coagulant-containing polymer films that are used as tissue sealants. In particular, it relates to a polymer film that incorporates fibrinogen and thrombin in which the fibrinogen acts to attach the polymer film to the tissue.

BACKGROUND OF THE INVENTION

Wound dressings, tissue coatings, and tissue adhesives are examples of devices that serve to stop or prevent leakage of blood and other bodily fluids. These dressings can serve to seal open wounds, prevent infection, and so on. Many types of wound dressings and tissue adhesives known in the literature incorporate one or more coagulants such as fibrinogen.

Numerous examples are known in the literature of coagulant-containing tissue sealant compositions. U.S. Pat. No. 5,631,011 discloses a tissue treatment composition comprising fibrin or fibrinogen and a polymer that is biodegradable and biocompatible and capable of forming a viscous aqueous solution. The composition acts as a glue to bind tissue, e.g. a cut and sutured blood vessel. U.S. Pat. No. 6,699,844 discloses a fibrin-containing tissue sealant that also contains a derivative of hyaluronic acid. U.S. Pat. No. 6,162,241 discloses a hemostatic tissue sealant comprising a biocompatible, biodegradable hydrogel tissue sealant comprising crosslinkable groups having incorporated therein an effective amount of a hemostatic agent to stop the flow of blood from tissue in a medically acceptable period of time.

U.S. Pat. No. 6,056,970 discloses compositions that comprise hemostatic agents and optionally bioabsorbable polymers. A fibrous precipitate comprising a hemostatic agent such as thrombin is prepared by injecting an aqueous solution of the hemostatic agent into a non-aqueous solvent. The precipitate may be mixed with a second precipitate comprising a second hemostatic agent such as fibrinogen. The precipitates are then high-shear mixed to form a solution in the non-aqueous solvent and pressed, using known papermaking technology, to form a paper-like fibrous structure throughout which the hemostatic agents are distributed. Upon contact with a fluid, the hemostatic agents are activated and the composition acts as a hemostatic patch.

Methods are also known in the art for preparing compositions that can release a pharmaceutically effective agent such as a hemostatic agent from a polymeric matrix. For example, U.S. Pat. No. 6,194,005 discloses a method in which a powdered pharmaceutically effective agent is sprayed onto a warm lipid matrix, which thereby coats the agent. U.S. Pat. No. 6,579,537 discloses a method for producing inter alia a fibrinogen composition using a polyalkylene glycol. The basic method comprises producing a solution of fibrinogen and fibronectin and precipitating the fibrinogen and fibronectin by adding a polyalkylene glycol and an amino acid. U.S. Pat. Appl. Pub. No. 2012/0121532 discloses a method for preparing a dry and stable hemostatic composition. A dry hemostatic agent is mixed with a dry polymeric component in proportions such that on addition of an appropriate diluent (e.g. water), a polymeric matrix (e.g. a hydrogel) into which the hemostatic agent is incorporated.

Also known in the art are non-fibrous polymer films or coatings that incorporate a hemostatic agent such as thrombin. For example, U.S. Pat. Appl. Pub. No. 2007/0059346 discloses a film containing nitroglycerin and possibly other therapeutic agents; the film is made of a water-soluble polymer that can dissolve in the mouth of a patient.

Hemostatic wound dressings that incorporate fibrinogen are also known in the art. U.S. Pat. No. 7,189,410 discloses a layered fibrin sealant bandage comprising a backing layer and a hemostatic component layer containing fibrinogen, the fibrinogen acting to produce a clot when the bandage is applied to a wound. A family of patents that includes inter alia U.S. Pat. No. 6,054,122 discloses fibrin sealant bandages that comprise an occlusive backing, an adhesive layer on the wound-facing surface of the backing, and a layer of dry hemostatic materials (fibrinogen, thrombin, and $Ca^{2+}$ and/or Factor XIII as necessary). The dry materials adhere to, but are not incorporated into, the adhesive layer and are exposed at the time of use. U.S. Pat. Appl. Pub. No. 2006/0155235 discloses a hemostatic compression bandage that bandage comprises a flexible backing element, a powdered hemostatic substance, and a flexible film element. In this bandage, the hemostatic substance remains as a free powder. Immediately prior to use, the flexible film element is peeled away, exposing the powder, which is then placed directly on the wound. International (PCT) Pat. Appl. Pub. No. WO2006/044882 discloses a reinforced absorbable multilayered hemostatic wound dressing that comprises a first absorbable nonwoven fabric comprising aliphatic polyester polymers, copolymers, or blends thereof reinforced by a second absorbable woven or knitted fabric comprising oxidized regenerated cellulose and thrombin and fibrinogen. U.S. Pat. Appl. Pub. No. 2011/0288462 discloses a hemostatic wound dressing that comprises a super-absorbent polymer and a hemostatic agent.

In the compositions and dressings known in the literature, the fibrin sealant component serves the dual role of adhering to the tissue and as a coagulant. In hemostatic dressings known in the literature, the backing is used to support the fibrinogen, which must therefore be used in relatively large quantities. There thus remains a need for a tissue sealant or adhesive device that uses fibrin to cause the film component to adhere to the tissue but in which the film component, rather than the fibrin component, is the primary tissue sealing component.

SUMMARY OF THE INVENTION

The invention herein disclosed is designed to meet this long-felt need. In particular, a tissue adhesive patch is disclosed, that comprises a backing made of a biocompatible polymer, which acts to seal tissue into or out of which fluid is leaking, and a hemostatic agent (e.g. a fibrinogen sealant) incorporated into the backing. In preferred embodiments of the invention, the hemostatic agent acts to bind the backing to the tissue rather than to seal the tissue. The invention herein disclosed additionally comprises methods of preparation and use of the tissue adhesive patch.

It is therefore an object of this invention to disclose a fibrinogen-based tissue adhesive patch, comprising a backing made from a film made of a biocompatible polymer and a fibrinogen sealant incorporated into said backing such that said fibrinogen sealant remains partially exposed on said at least one surface. In preferred embodiments of the invention, said adhesive patch does not include any interpenetrating polymer network; any mesh, woven, or non-woven component; or any material made by methods of paper-making technology.

It is a further object of this invention to disclose such a fibrinogen-based tissue adhesive patch, wherein said backing comprises a film made of a biocompatible polyurethane polymer comprising units of a biocompatible polymer connected by isocyanate linkages. In some preferred embodiments of the invention, said biocompatible polymer is selected from the group consisting of polyethylene glycol-polycaprolactone copolymers; polyethylene glycol-DL-lactide copolymers; and polyethylene glycol-polycaprolactone-DL-lactide copolymers. In some preferred embodiments of the invention in which said backing comprises a film made of a biocompatible polyurethane polymer comprising units of a biocompatible polymer connected by isocyanate linkages, wherein said polyurethane linkages are the product of reaction between two biocompatible polymer units and an aliphatic diisocyanate. In some particularly preferred embodiments of the invention, said aliphatic diisocyanate is hexamethylene diisocyanate (HDI).

It is a further object of this invention to disclose a tissue adhesive patch as defined in any of the above, wherein said backing is characterized by at least one physical characteristic selected from the group consisting of: a Young's Modulus of between 50 MPa and 200 MPa; a tensile strength of between 5 MPa and 15 MPa; a melting point of between 45° C. and 52° C.; a water uptake of between 30% and 50%; and, a breakdown time in water (half-life) of between 15 days and 30 days.

It is a further object of this invention to disclose a tissue adhesive patch as defined in any of the above, wherein said patch is configured such that contact between said adhesive patch, a tissue, and a fluid, activates said fibrinogen sealant such that said fibrinogen sealant acts to attach said backing to said tissue.

It is a further object of this invention to disclose a tissue adhesive patch as defined in any of the above, wherein said fibrinogen sealant is incorporated into said at least one surface to a depth of between about 20 microns and about 60 microns.

It is a further object of this invention to disclose a tissue adhesive patch as defined in any of the above, wherein said fibrinogen sealant is not distributed throughout said backing.

In some embodiments of the invention, said fibrinogen sealant comprises fibrinogen, thrombin, and $CaCl_2$. In some embodiments of the invention, said fibrinogen sealant comprises fibrinogen but does not comprise thrombin. In some embodiments of the invention, said fibrinogen sealant consists essentially of fibrinogen, thrombin, and $CaCl_2$. In some embodiments of the invention, said fibrinogen sealant consists essentially of fibrinogen.

It is a further object of this invention to disclose such a tissue adhesive patch, wherein said tissue adhesive patch does not comprise any hemostatic agent in the form of a free powder.

It is a further object of this invention to disclose such a tissue adhesive patch as defined in any of the above, wherein said biocompatible polymer is non-permeable.

It is a further object of this invention to disclose such a tissue adhesive patch as defined in any of the above, wherein said biocompatible polymer is selected from the group consisting of polyethylene glycol-polycaprolactone copolymers; polyethylene glycol-DL-lactide copolymers; and polyethylene glycol-polycaprolactone-DL-lactide copolymers.

It is a further object of this invention to disclose such a tissue adhesive patch as defined in any of the above, wherein said backing has a thickness of about 200 µm. It is a further object of this invention to disclose such a tissue adhesive patch as defined in any of the above, wherein said backing has a thickness of about 100 µm.

It is a further object of this invention to disclose such a tissue adhesive patch as defined in any of the above, wherein said patch comprises between 0.5 mg and 8 mg of fibrinogen and between 20 IU and 1000 IU of thrombin per square centimeter of film. In some embodiments of the invention, said fibrinogen sealant comprises fibrinogen, thrombin, and $CaCl_2$ in a ratio of 425:5:11 by weight.

It is a further object of this invention to disclose such a tissue adhesive patch as defined in any of the above, wherein said fibrinogen sealant additionally comprises at least one additive. In some preferred embodiments of the invention, said additive is selected from the group consisting of additives for extending the adhesion half-life of said film, pharmaceutically active agents, and analgesics. In some preferred embodiments of the invention, said additive is a plasmin inhibitor for extending the adhesion half-life of said film. In some preferred embodiments of the invention, said additive is a pharmaceutically active agent for targeted or controlled release.

It is a further object of this invention to disclose a method for producing a fibrinogen-based tissue adhesive patch, wherein said method comprises: casting a polymer film from a biocompatible polymer; softening said polymer film; placing a fibrinogen sealant on at least one surface of said polymer film; and pressing said polymer film until at least a portion of said fibrinogen sealant is incorporated into the surface of said polymer film.

It is a further object of this invention to disclose such a method, wherein said biocompatible polymer is selected from the group consisting of polyethylene glycol-polycaprolactone copolymers; polyethylene glycol-DL-lactide copolymers; and polyethylene glycol-polycaprolactone-DL-lactide copolymers. In some preferred embodiments of the method, said step of casting a polymer film comprises casting a polymer film from a biocompatible crosslinked polyurethane polymer comprising a units of a biocompatible block copolymer connected by polyurethane linkages, said biocompatible block copolymer selected from the group consisting of polyethylene glycol-polycaprolactone copolymers; polyethylene glycol-DL-lactide copolymers; and polyethylene glycol-polycaprolactone-DL-lactide copolymers.

In some embodiments of the method, said step of placing a fibrinogen sealant on at least one surface of said polymer film comprises placing a fibrinogen sealant comprising fibrinogen, thrombin, and $CaCl_2$ on at least one surface of said polymer film. In some embodiments of the method, said step of placing a fibrinogen sealant on at least one surface of said polymer film comprises placing a fibrinogen sealant comprising fibrinogen but not comprising thrombin on at least one surface of said polymer film. In some embodiments of the method, said step of placing a fibrinogen sealant on at least one surface of said polymer film comprises placing a fibrinogen sealant consisting essentially of fibrinogen, thrombin, and $CaCl_2$ on at least one surface of said polymer film. In some embodiments of the method, said step of placing a fibrinogen sealant on at least one surface of said polymer film comprises placing a fibrinogen sealant consisting essentially of fibrinogen on at least one surface of said polymer film.

It is a further object of this invention to disclose such a method, wherein said biocompatible polymer is non-permeable.

It is a further object of this invention to disclose the method as defined in any of the above, wherein said step of casting a polymer film comprises preparing a solution of a dry polymer in an organic solvent and evaporating said organic solvent. In some preferred embodiments of the invention, said step of preparing a solution of dry polymer in organic solvent comprises preparing a 24% (w/v) solution. In some preferred embodiments of the invention, said step of preparing a solution of dry polymer in organic solvent comprises preparing a solution of dry polymer in an organic solvent selected from the group consisting of THF, chloroform, dioxane, acetone, 1-methyl-2-pyrrolidinone, DMF, and DMA. In some particularly preferred embodiments of the invention, said step of preparing a solution of dry polymer in organic solvent comprises preparing a solution of dry polymer in THF. In some embodiments of the invention, it further comprises covering said solution during at least part of the time that said step of evaporating said organic solvent is taking place.

It is a further object of this invention to disclose the method as defined in any of the above, wherein said step of casting a polymer film comprises casting a polymer film of thickness of about 100 µm. It is a further object of this invention to disclose the method as defined in any of the above, wherein said step of casting a polymer film comprises casting a polymer film of thickness of about 200 µm.

It is a further object of this invention to disclose the method as defined in any of the above, wherein said step of casting a polymer film comprises casting said polymer film on a smooth flat surface. In some preferred embodiments of the invention, said step of placing said polymer film on a smooth flat surface comprises placing said polymer film on a surface made of a material selected from the group consisting of glass, silicone, and polytetrafluoroethylene. In some particularly preferred embodiments of the invention, said step of placing said polymer film on a smooth flat surface comprises placing said polymer film on a glass surface. In some embodiments of the invention, the method further comprises a step of removing said polymer film from said smooth flat surface following said step of pressing said polymer film. In some embodiments of the invention, it further comprises a step of placing said polymer film in a freezer following said step of pressing said polymer and prior to said step of removing said polymer film from said smooth flat surface. In some preferred embodiments of the invention, said step of placing said polymer film in a freezer comprises placing said polymer film in a freezer at a temperature of between −25° C. and −15° C.

It is a further object of this invention to disclose the method as defined in any of the above, wherein said step of softening said polymer film comprises heating said polymer film until said polymer film softens. In some embodiments of the invention, said step of heating said polymer film until said polymer film softens comprises heating said polymer film to a temperature of between 55° C. and 60° C. In some embodiments of the invention, said step of pressing said polymer film is followed by a step of cooling said polymer film sufficiently slowly that the film returns substantially to its original morphology.

It is a further object of this invention to disclose the method as defined in any of the above, wherein said step of pressing said polymer film until at least a portion of said fibrinogen sealant is incorporated into a surface of said polymer film comprises pressing said polymer film until said fibrinogen sealant is incorporated into said at least one surface to a depth of between 20 µm and 60 µm.

It is a further object of this invention to disclose the method as defined in any of the above, wherein said method does not include any step of distributing said fibrinogen sealant throughout said backing.

It is a further object of this invention to disclose such a method, wherein said step of softening said polymer film comprises softening said polymer film by using residual solvent.

It is a further object of this invention to disclose the method as defined in any of the above, wherein said step of placing a fibrinogen sealant comprising fibrinogen, thrombin, and CaCl$_2$ on at least one surface of said polymer film comprises placing a sufficient quantity of said fibrinogen sealant on at least one surface of said polymer film sufficient to provide between 0.5 mg and 8 mg of fibrinogen and between 20 IU and 1000 IU of thrombin per square centimeter of film.

It is a further object of this invention to disclose the method as defined in any of the above, wherein said step of placing a fibrinogen sealant comprising fibrinogen, thrombin, and CaCl$_2$ on at least one surface of said polymer film comprises placing a fibrinogen sealant comprising fibrinogen, thrombin, CaCl$_2$ and at least one additive on at least one surface of said polymer film. In some embodiments of the invention, said step of placing a fibrinogen sealant comprising fibrinogen, thrombin, CaCl$_2$ and at least one additive on at least one surface of said polymer film comprises placing a fibrinogen sealant comprising fibrinogen, thrombin, CaCl$_2$ and at least one additive selected from the group consisting of additives for extending the adhesion half-life of said polymer film, pharmaceutically active agents, and analgesics on at least one surface of said polymer film. In some preferred embodiments of the invention, said step of placing a fibrinogen sealant comprising fibrinogen, thrombin, CaCl$_2$ and at least one additive on at least one surface of said polymer film comprises placing a fibrinogen sealant comprising fibrinogen, thrombin, CaCl$_2$ and a plasmin inhibitor on at least one surface of said polymer film. In some preferred embodiments of the invention, said step of placing a fibrinogen sealant comprising fibrinogen, thrombin, CaCl$_2$ and at least one additive on at least one surface of said polymer film comprises placing a fibrinogen sealant comprising fibrinogen, thrombin, CaCl$_2$ and at least one pharmaceutically active agent for targeted or sustained release on at least one surface of said polymer film.

It is a further object of this invention to disclose the method as defined in any of the above, further comprising providing a fibrinogen sealant comprising fibrinogen, thrombin, and CaCl$_2$ in the form of a powder. In some embodiments of the invention, said step of placing a fibrinogen sealant comprising fibrinogen, thrombin, and CaCl$_2$ on at least one surface of said polymer film comprises placing said powder on said at least one surface by a method selected from the group consisting of sprinkling, spreading, spraying, and spraying a suspension of said powder in an organic solvent.

It is a further object of this invention to disclose the method as defined in any of the above, further comprising a step of placing a smooth material having a flat surface on top of said film prior to said step of pressing said polymer film.

It is a further object of this invention to disclose the method as defined in any of the above, wherein said step of pressing said polymer film comprises pressing said polymer film according to a programmed compression procedure. In some embodiments of the invention, said step of pressing said polymer film according to a programmed compression procedure comprises pressing said polymer film with a force that continuously increases to a maximum of about 50 N.

It is a further object of this invention to disclose the method as defined in any of the above, further comprising a step of removing excess fibrinogen sealant from said polymer film following said step of pressing said polymer film.

It is a further object of this invention to disclose a tissue adhesive patch as defined in any of the above, produced by a method as defined in any of the above.

It is a further object of this invention to disclose a method of treating a leak of fluid into or out of a body part, comprising applying a tissue adhesive patch as defined in any of the above to said body part such that contact with said fluid activates said fibrinogen sealant whereby said activated fibrinogen sealant attaches said polymer backing to said body part, thereby sealing said body part. In some embodiments of the method of treating a leak of fluid into or out of a body part, said body part is selected from the group consisting of arteries and organs. In some embodiments, said step of applying a tissue adhesive patch comprises manually pressing said patch on the surface of said body part.

It is a further object of this invention to disclose a method of treating a leak of fluid into or out of a body part, comprising applying a tissue adhesive patch prepared by the method as defined in any of the above to said body part such that contact with said fluid activates said fibrinogen sealant whereby said activated fibrinogen sealant attaches said polymer backing to said body part, thereby sealing said body part. In some embodiments of the method of treating a leak of fluid into or out of a body part, said body part is selected from the group consisting of arteries and organs. In some embodiments, said step of applying a tissue adhesive patch comprises manually pressing said patch on the surface of said body part.

It is a further object of this invention to disclose a method of treating a leak of fluid into or out of a body part, comprising applying thrombin to said body part and applying a tissue adhesive patch as defined in any of the above in which said fibrinogen-based sealant comprises or consists essentially of fibrinogen to said body part, thereby causing said tissue adhesive patch to adhere to said affected artery or organ, thereby sealing said artery or organ. In some embodiments of the method of treating a leak of fluid into or out of a body part, said body part is selected from the group consisting of arteries and organs. In some embodiments, said step of applying a tissue adhesive patch comprises manually pressing said patch on the surface of said body part.

It is a further object of this invention to disclose such a method of treating a leak of fluid into or out of a body part as defined in any of the above, wherein said leak of fluid is selected from the group consisting of arterial bleeding; organ tissue bleeding; bile anastomosis; cerebrospinal fluid leak; dura leak; and air leak in damaged lung tissue.

It is a further object of this invention to disclose the use of a tissue adhesive patch as defined in any of the above in the treatment of a leak of fluid into or out of a body part.

It is a further object of this invention to disclose such a use, wherein said leak of fluid is selected from the group consisting of arterial bleeding; organ tissue bleeding; bile anastomosis; cerebrospinal fluid leak; dura leak; and air leak in damaged lung tissue.

BRIEF DESCRIPTION OF THE DRAWINGS

The invention will now be described with reference to the drawings, wherein:

FIGS. 4A-4C presents graphs showing the tensile modulus of wet polyethylene-caprolactone-lactide (PECALA) films of varying compositions in comparison to a PECA film with an EO/CL ratio of 2.0;

DETAILED DESCRIPTION OF THE PREFERRED EMBODIMENTS

Figure 1:
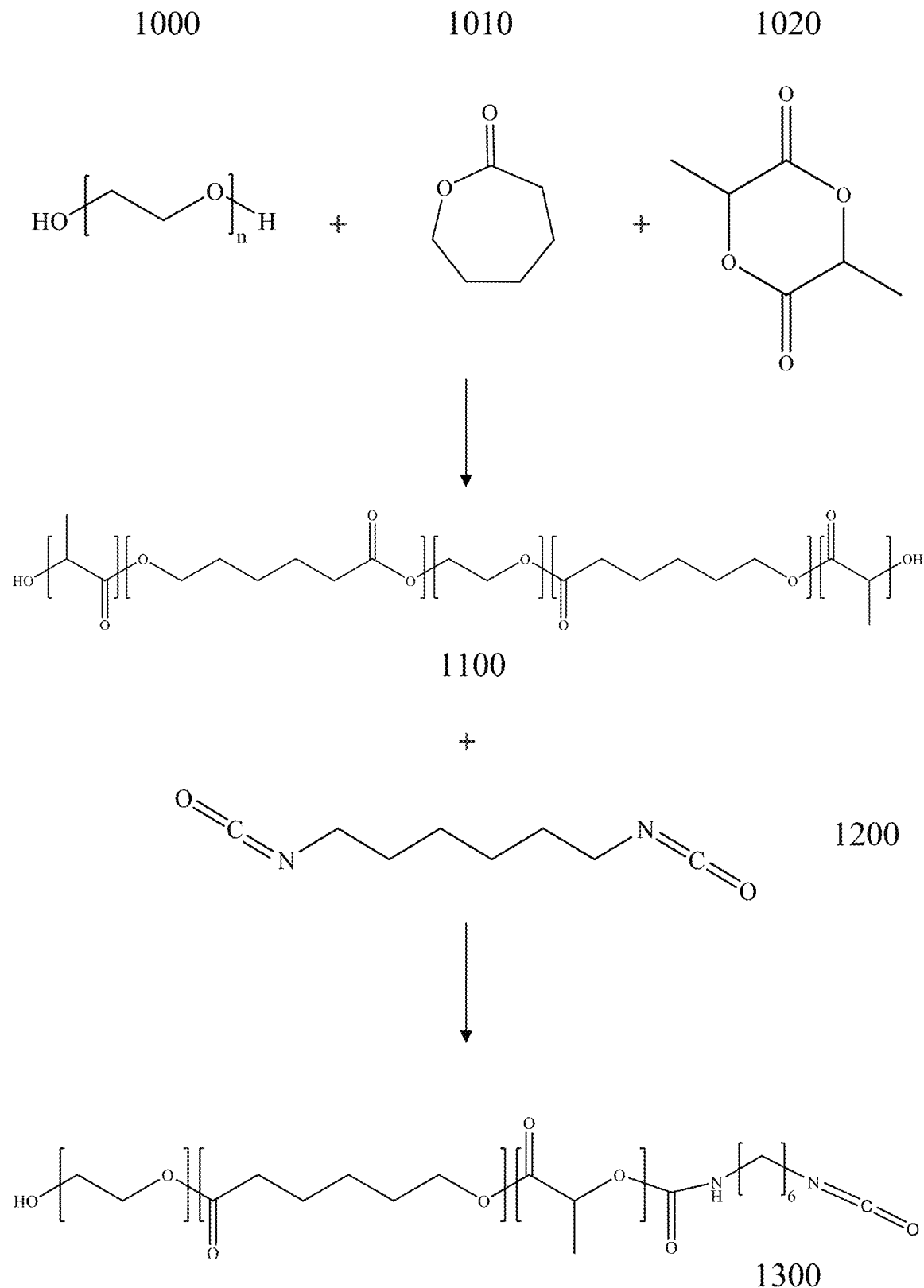
FIG. 1 presents a synthetic strategy for preparation of a PECALA biocompatible polyurethane polymer used as a backing in one exemplary non-limiting embodiment of the hemostatic patch herein disclosed.
Figure 2A:
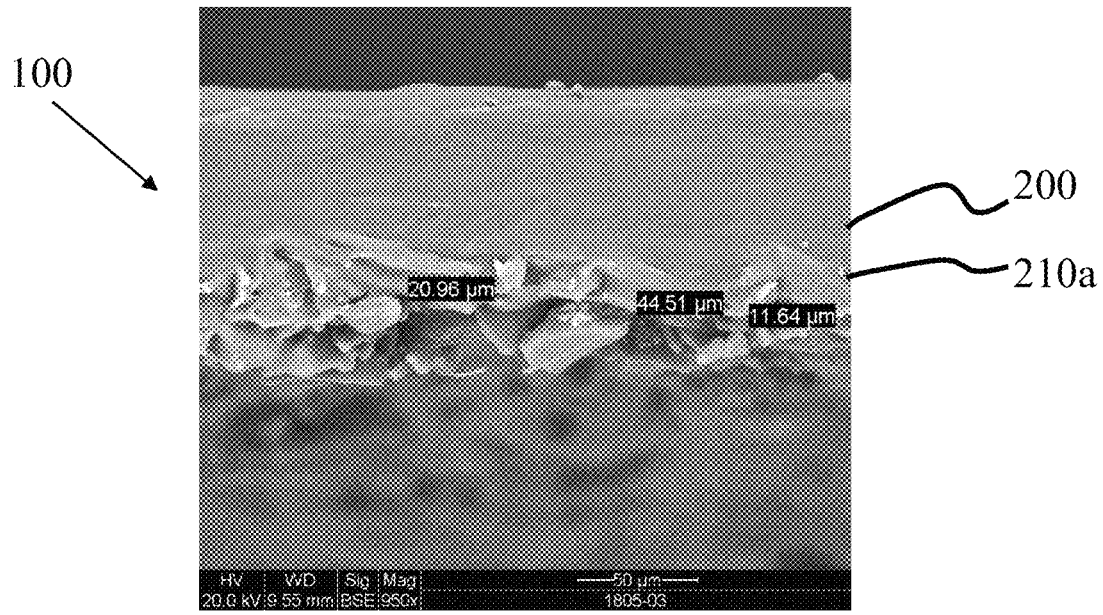
FIGS. 2A-2D are four SEM photographs that illustrate the incorporation of the fibrinogen sealant into the polymer backing in one non-limiting exemplary embodiment of the invention disclosed herein.
Figure 2B:
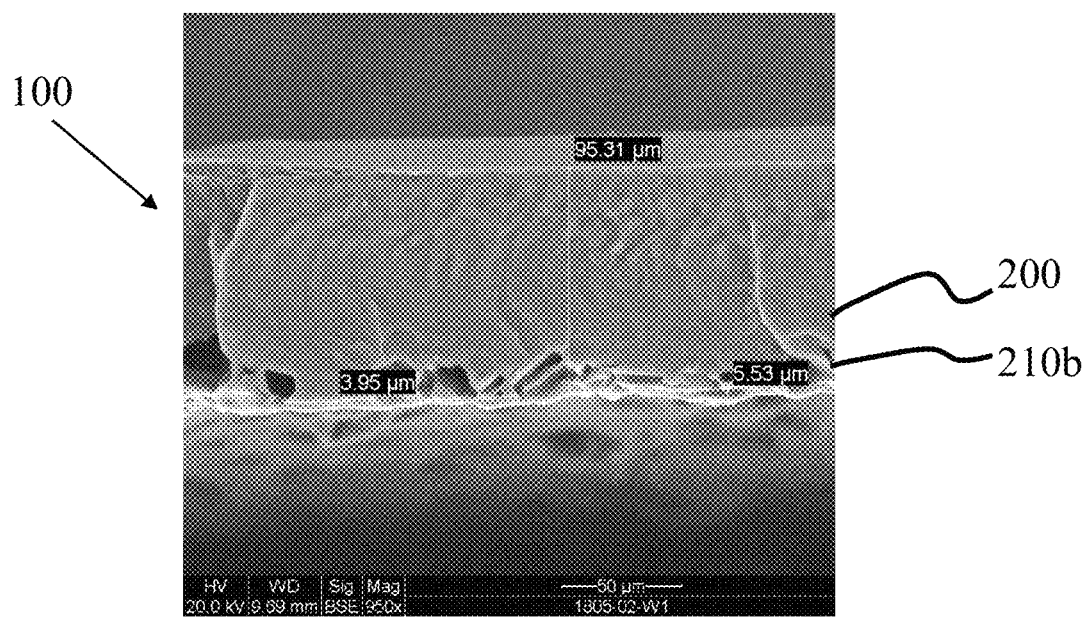
Figure 2C:
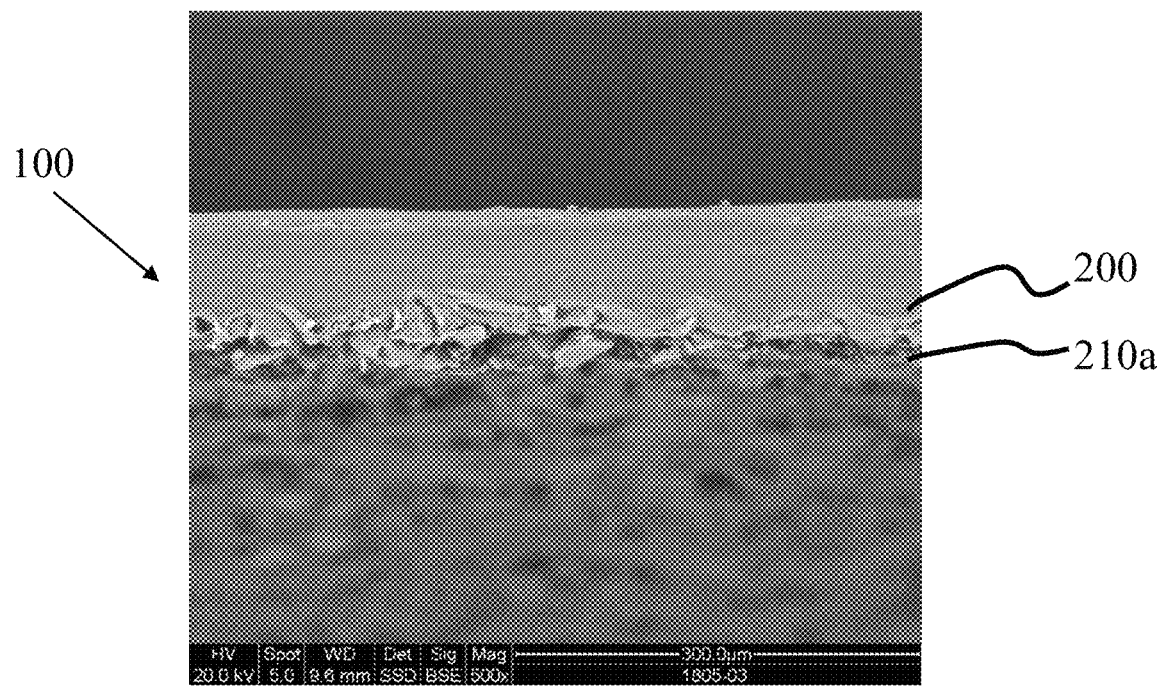
Figure 2D:
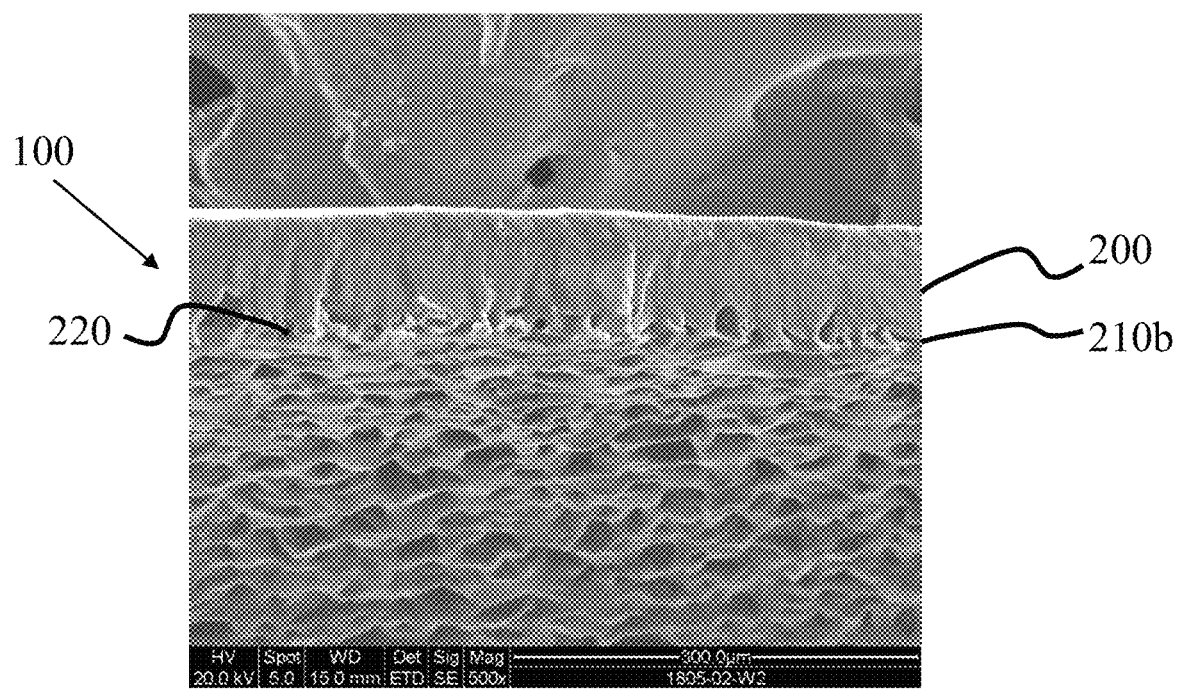

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

As used herein, the terms "PEG" and "PEO" refer to polyethylene glycol and polyethylene oxide, respectively, and are used interchangeably.

As used herein, the term "PECA" refers to a biocompatible polyurethane polymer comprising PEG-polycaprolactone (PCL) diblock copolymer units connected by urethane linkages. When the term PECA is followed by a number, the number indicates the ratio of ethylene oxide repeat units in the PEG segment to caprolactone repeat units in the PCL segment. The greater the number, the more hydrophilic the PECA copolymer will be.

As used herein, the term "PELA" refers to a biocompatible polyurethane polymer comprising PEG-lactide diblock copolymer units connected by urethane linkages; lactide is the cyclic diester of lactic acid.

As used herein, the term "PECALA" refers to a biocompatible polyurethane polymer comprising PEG-PCL-lactide triblock copolymer units connected by urethane linkages. When the term PECALA is followed by two numbers, the first indicates the ratio of hydrophilic (PEG) to hydrophobic (PCL and lactide) repeat units, and the second to the number of lactide units per triblock flank.

As used herein, the term "HDI" refers to hexamethylene diisocyanate (1,6-diisocyanatohexane).

As used herein, the abbreviation "IPN" stands for "interpenetrating network."

As used herein, the term "about," when applied to numerical quantities, refers to a range of ±25% of the nominal value.

As used herein, when a particulate material is described as "incorporated" into a solid or semisolid material, unless stated otherwise, the term "incorporated" is used to refer to partial embedding in which the particles are partially within the second material and partially exposed above its surface.

In preferred embodiments, the backing of the fibrinogen-based tissue adhesive of the present invention comprises a film made from a biocompatible polymer into the surface of which a fibrin-based sealant is incorporated. In more preferred embodiments, the biocompatible polymer film is made from a non-permeable material. In preferred embodiments, the biocompatible polymer film is made of a thermoelastic polyurethane comprising biocompatible polymer units connected by urethane linkages. In more preferred embodiments of the invention, the biocompatible polymer film comprises biocompatible polymer units linked by reaction with an aliphatic diisocyanate to produce a polyurethane. In yet more preferred embodiments of the invention, the aliphatic diisocyanate is hexmethylene diisocsyanate. In still more preferred embodiments of the invention, the ratio of diisocyanate to copolymer side chains is 1:1. In the most preferred embodiments of the invention, the biocompatible polymer film is made from a polymer selected from the group consisting of PELA, PECA, and PECALA.

In order to assist a person of ordinary skill in the art to make and use the invention, and to assist in the understanding of the structure of the polymers used in preferred embodiments of the invention, reference is now made to FIG. 1, which shows a non-limiting exemplary synthetic strategy for preparation of PECALA, one polymer that the inventors have found is particularly useful for preparation of the hemostatic patches disclosed herein. In the first step, PEG (1000), ε-caprolactone (1010) and lactide (1020) are copolymerized to form macrodiol ester triblock copolymer 1100. Units of copolymer 1100 are then connected by reaction with diisocyanate 1200 to form the final polyurethane polymer product, PECALA (1300). In preferred embodiments of the invention, reaction with HDI (the diisocyanate shown in FIG. 1) is used to produce the polyurethane linkages, but any diisocyanate that will produce a biocompatible polymer with the desired physical properties such as tensile strength and breakdown time may be used. The polymer used to produce the backing may be prepared by any method known in the art. It is emphasized that the foregoing description of the synthesis of PECALA is given solely in order that a person of ordinary skill in the art will understand the general structure of the polyurethane polymers preferably used in the invention. Any biocompatible polymer with the desired physical and chemical properties may be used in the patches of the invention herein disclosed, and any backing made with such biocompatible polymers is considered by the inventors to be within the scope of the invention regardless of the method used to synthesize the polymer. Furthermore, in preferred embodiments of the method of preparation of the hemostatic tissue adhesive patches described in detail below, the method does not include the synthesis of the polymer used as the backing, but rather begins with the casting of the polymer film. Thus, embodiments of the hemostatic patch, the method for making it, and the method for using it, in which the biocompatible polymer used as the backing is synthesized by another method, or obtained commercially, are considered by the inventors to be within the scope of the invention.

The thermoelastic polyurethane polymers used as backing material in preferred embodiments of the invention herein disclosed have ideal properties for their use as backing material for the hemostatic patch. Not only are they biocompatible and biodegradable with a relatively rapid breakdown time, they are characterized by high tensile strength, high toughness, and high elongation at break.

In contrast to similar tissue adhesive films known in the art, such as those disclosed, for example, in U.S. Pat. No. 6,495,127, in preferred embodiments of the invention herein disclosed, the biocompatible polymer film does not comprise any IPN.

In its most basic formulation, the sealant consists essentially of fibrinogen, thrombin, and $CaCl_2$. In other embodiments, the sealant comprises fibrinogen, thrombin, and $CaCl_2$, and may contain one or more additional components. Non-limiting examples of these additional components include plasmin inhibitors, which serve to extend the adhesion half-life; pharmaceutically active agents; and analgesics.

In some embodiments, the sealant contains fibrinogen, thrombin, and $CaCl_2$ in a ratio of 425:5:11 by weight. This ratio corresponds to ~200 mg pure fibrinogen, ~250 IU thrombin, and 11 mg $CaCl_2$ per 441 mg of the mixture. In other embodiments of the invention, no $CaCl_2$ is added to the adhesive, the amount of $CaCl_2$ present in the thrombin as received from commercial suppliers being sufficient to act as a cofactor for the enzymatic activity of the thrombin. In preferred embodiments of the invention, the sealant is a microparticulate powder, and the amount of sealant incorporated into the film is sufficient to provide a concentration of 0.5-8 mg of fibrin and 20-10000 IU of thrombin per square centimeter of film. This concentration corresponds to about 3-6 mg of the 425:5:11 mixture described above. In more preferred embodiments, the concentration of fibrinogen in the adhesive is between 0.5 and 6 mg per square centimeter of film. In still more preferred embodiments, the adhesive provides about 4 mg fibrinogen and about 2-5 IU of thrombin per square centimeter of film. In the most preferred embodiments, the concentration of fibrinogen in the adhesive is less than 2 mg per square centimeter of film.

In some embodiments of the invention, the patch is provided as a two-component system. In these embodiments, the sealant does not contain any thrombin. In some of these embodiments, the sealant consists essentially of fibrinogen; in others, the sealant comprises fibrinogen, but may contain other components, non-limiting examples of which include plasmin inhibitors, which serve to extend the adhesion half-life; pharmaceutically active agents; and analgesics. In the embodiments in which the patch is provided as a two-component system, thrombin is provided separately; as a non-limiting example, it can be provided in a solution. In these embodiments of the invention, the thrombin component is applied to the affected body part, e.g. by spraying, and the patch containing the fibrinogen-based sealant is then applied to the affected body part. The fibrinogen component of the sealant and the thrombin applied to the affected body part then react to form fibrin, which binds the patch to the affected body part.

It is emphasized that in contrast to hemostatic patches and dressings known in the art, preferred embodiments of the tissue adhesive of the present invention do not include a mesh, woven, or non-woven component or any kind of IPN; the polymer film, not the fibrinogen sealant, acts to seal the tissue. The fibrinogen acts solely to attach the polymer film to the tissue upon activation by contact with a fluid, e.g. a body fluid leaking out of or into the tissue to which the sealant patch is being applied. In contrast to tissue sealant patches known in the art, preferred embodiments of the present invention do not comprise woven or non-woven fabrics or materials made by techniques known in paper-making technology. The present invention discloses in its preferred embodiments a tissue adhesive that comprises a single layer of polymer film into which fibrinogen and thrombin are incorporated, in contrast to multilayer hemostatic dressings known in the art; embodiments of the invention herein disclosed in which additional layers are added for ease of handling or storage are not excluded from the scope of the present invention, however. Furthermore, in the present invention, the fibrinogen sealant component is physically incorporated into the polymer film to form a single integrated unit; as described below, in preferred embodiments, the patch is prepared by mechanically pressing the hemostatic agent into the surface of the film. Thus, in contrast to hemostatic patches and dressings known in the art, in which the hemostatic agent is neither present as a free powder, nor is it distributed throughout the polymer backing. Rather, the hemostatic agent is present in the dressing in a layer that extends on the order of tens of microns beneath the surface of the polymer backing. In preferred embodiments, this layer extends approximately 20-60 μm below the surface of the backing. In more preferred embodiments, the layer of hemostatic agent extents 40-60 μm below the surface of the backing.

Reference is now made to FIG. 2, which presents SEM photographs of one non-limiting embodiment of the hemostatic patch disclosed herein. FIG. 2A illustrates a cross-sectional view of a patch 100 of the instant invention. The patch includes a backing layer 200 that comprises PECALA film and has, in the example shown, a thickness of approximately 90-100 μm, and a layer of fibrin-containing sealant (210a). As can be seen in the photograph, the fibrin sealant layer extends into the PECALA film to a depth on the order of tens of microns, with no free powder remaining on the surface. FIG. 2B illustrates a patch after the fibrin-containing sealant has been activated by contact with fluid. As can be seen in the figure, the fibrin-containing sealant has dissolved to leave a layer (210b) approximately 5 μm thick, and "craters" (220) in the polymer film. FIGS. 2C and 2D present similar views but at approximately half the magnification. The "craters" left behind after activation of the fibrin-containing sealant are more clearly visible at this magnification (see FIG. 2D).

This configuration, namely, incorporation of a fibrinogen sealant material into a non-permeable polymer film backing, is to the inventors' knowledge previously unknown in the art, and thereby enables the tissue adhesive of the present invention to be used in a variety of unique applications. Non-limiting examples of applications in which the present invention can be used include covering traumatic and chronic wounds, stopping of arterial bleeding, stopping organ tissue bleeding, and sealing of other body fluids, for example, in treatment of bile anastomosis, cerebrospinal fluid and dura leaks, etc.

One important consideration for design of the patch is the physical properties of the polymer used to produce it. Some of the relationships between the composition of the polymer and its properties are given here as non-limiting examples of the types of polymer films that can be produced for use in the invention disclosed herein and thereby tailored to specific uses.

Table 1 summarizes some of the properties of PECA copolymers, as determined by GPC and $^1$H-NMR, as a function of the EO/CL ratio. The molecular weights reported in the table are true molecular weights and not polystyrene equivalents.

TABLE 1

| EO/CL | # of CL units per side | Molecular weight of CL flank [g/mol] | Number-average MW [g/mol] | Weight-average MW [g/mol] | Polydispersity | Degree of polymerization |
|---|---|---|---|---|---|---|
| 2.0 | 34.1 | 3,890 | 16,431 | 23,660 | 1.44 | 1.72 |
| 2.4 | 28.4 | 3,240 | 18,289 | 24,873 | 1.36 | 2.00 |
| 2.8 | 24.4 | 2,780 | 24,296 | 31,585 | 1.30 | 2.73 |
| 3.2 | 21.3 | 2,430 | 19,729 | 27,621 | 1.40 | 2.54 |
| 3.6 | 18.9 | 2,160 | 21,772 | 29,174 | 1.34 | 2.83 |
| 4.0 | 17.0 | 1,940 | 16,724 | 24,585 | 1.47 | 3.02 |
| 4.4 | 15.5 | 1,770 | 20,498 | 27,058 | 1.32 | 2.84 |
| 4.8 | 14.2 | 1,620 | 19,082 | 26,334 | 1.38 | 2.85 |
| 5.2 | 13.1 | 1,490 | 19,643 | 26,124 | 1.33 | 2.89 |

One property of PECA that makes it less preferred for some applications as a material for the backing of a hemostatic patch is its relatively slow rate of biodegradation; e.g., an in vitro test of a number of PECA films of varying compositions showed little degradation even after three months. Therefore, in some preferred embodiments of the invention in which rapid biodegradation is desired, PECALA films, which incorporate DL-lactide units into the CL segments, and hence biodegrade much more rapidly than PECA films, are used. Table 2 summarizes the properties, as determined by GPC and $^1$H-NMR spectroscopy, of PECALA films of various compositions.

TABLE 2

| Hydrophilic/Hydrophobic Ratio | # of lactide units per side | Number-average MW [g/mol] | Weight-average MW [g/mol] | Polydispersity | Degree of polymerization |
|---|---|---|---|---|---|
| 2.0 | 0.34 | 20,375 | 28,117 | 1.38 | 2.02 |
| 2.0 | 0.66 | 18,295 | 24,515 | 1.34 | 2.05 |
| 2.2 | 2.81 | 21,411 | 27,834 | 1.30 | 2.24 |
| 2.2 | 3.55 | 17,254 | 25,363 | 1.47 | 1.93 |

Figure 3A:
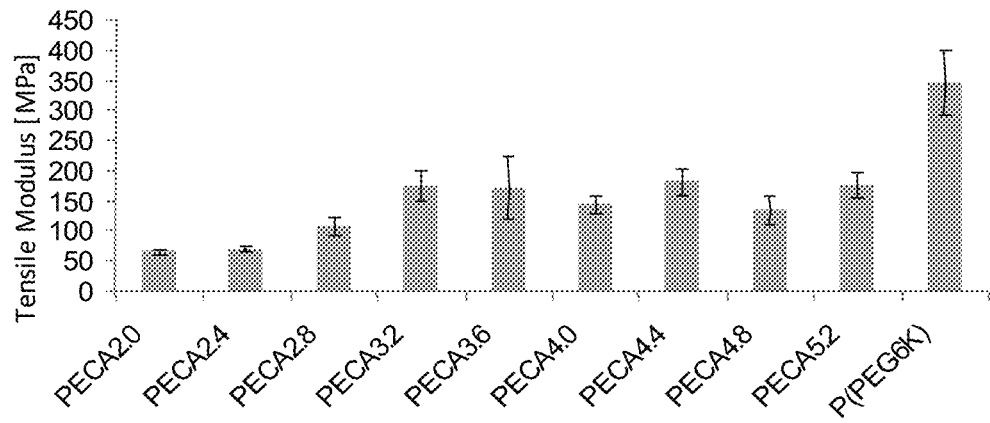
FIGS. 3A-3B presents a graph showing the tensile modulus of wet and dry films made from a polyethylene glycol-polycaprolactone copolymer (PECA) as function of the ratio of ethylene oxide (EO) to caprolactone (CL) units in the polymer.
Figure 3B:
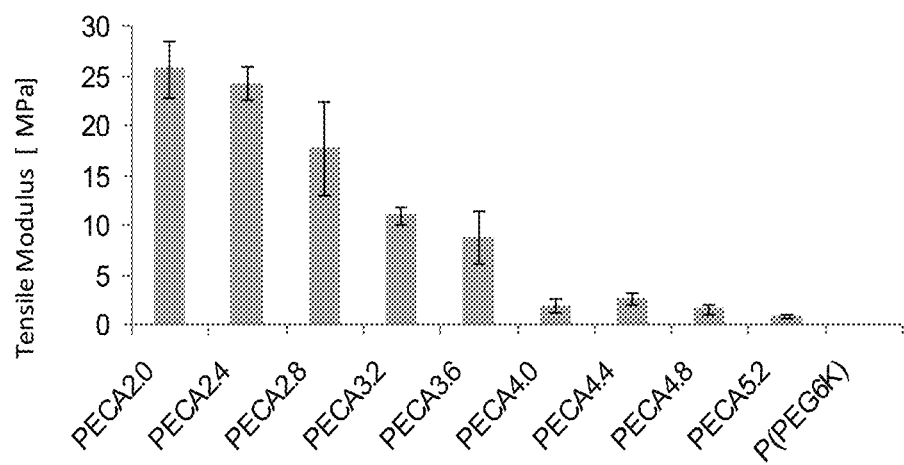

The mechanical properties of the polymer used to produce the film depend on the composition of the triblock and the molecular weight of the chain extended polymer, including the urethane linkages. Reference is now made to FIGS. 3A-3B, which presents graphs showing the results of measurements of tensile moduli of dry (FIG. 3A) and wet (FIG. 3B) PECA films as a function of the EO/CL ratio. The differences in the behavior of the dry and wet polymer films are primarily due to the ratio of the amount of hydrophilic PEG to hydrophobic PCL in the polymer films. Note that for the dry polymer films, the tensile modulus rises from ~60 MPa for PECA2.0 to ~160 MPa for PECA5.2, but appears to plateau at higher EO/CL ratios. In contrast, the tensile modulus of the wet polymer decreases with increasing EO/CL.

Reference is now made to FIG. 4A, which presents graphs showing results of measurements of the tensile moduli of several wet PECALA films. The tensile modulus of a wet PECA2.0 film is shown for comparison. Reference is now made to FIGS. 4B and 4C, which present graphs showing results of measurements of the tensile moduli and stress at break, respectively, for two different PECALA films in comparison to PECA2.8. These graphs show that PECALA's physical properties are similar to those of PECA.

Figure 5A:
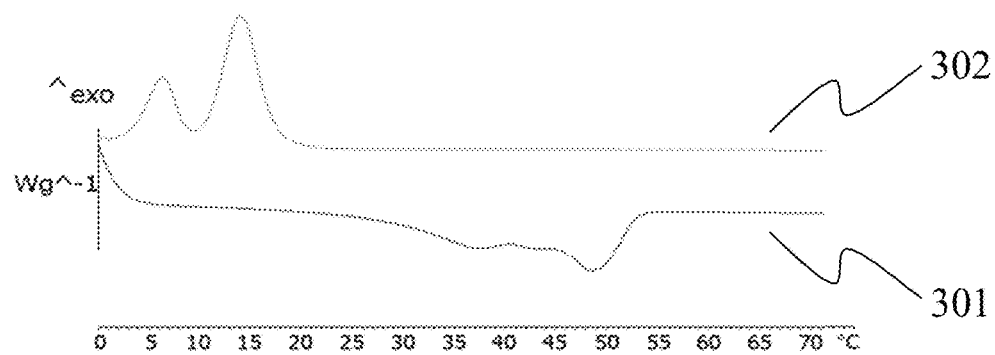
FIGS. 5A-5D shows DSC traces for wet and dry PECA films of different ethylene oxide/caprolactone ratios and for wet PECALA films of varying compositions.
Figure 5B:
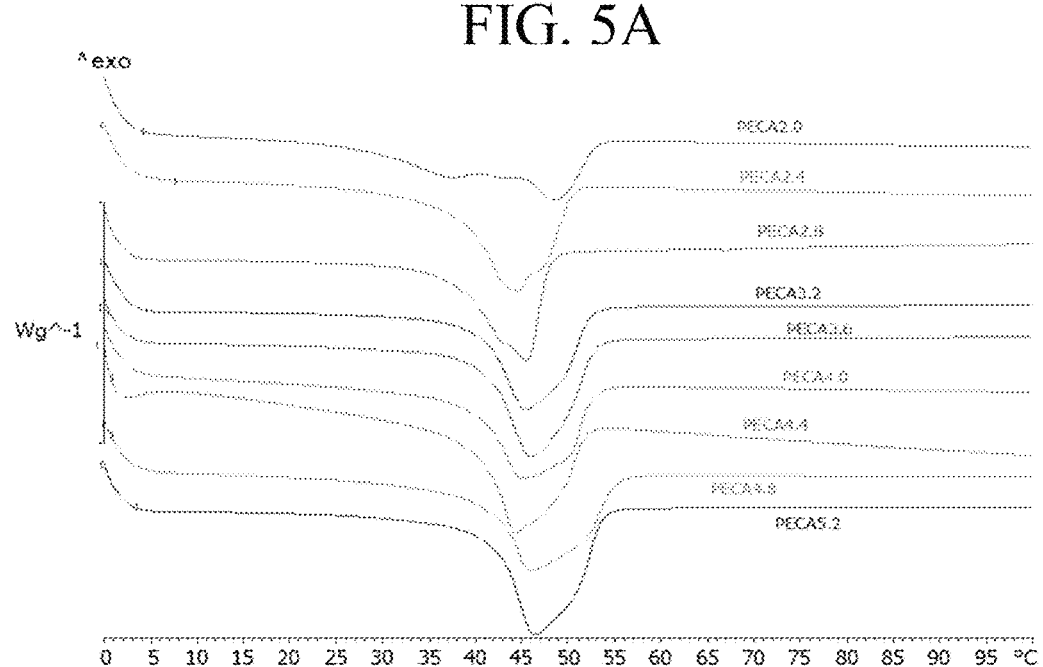
Figure 5C:
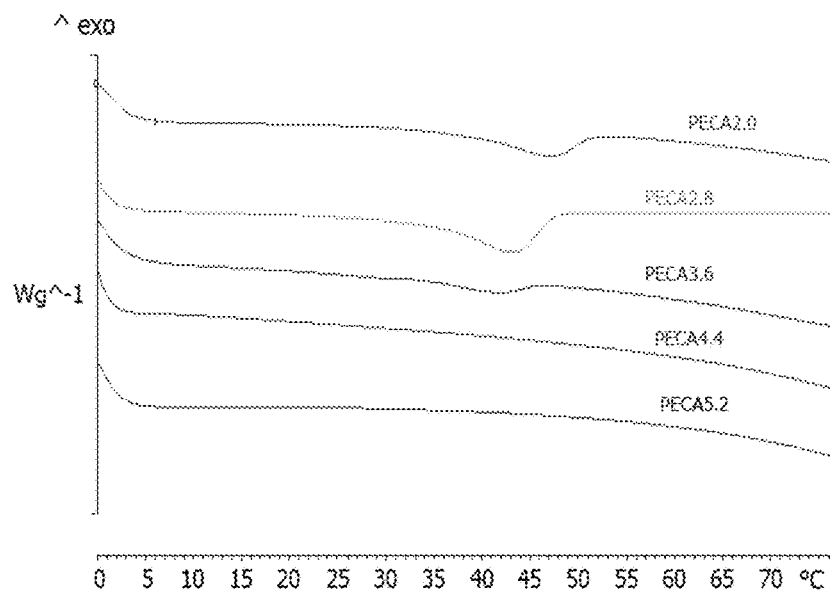

Reference is now made to FIGS. 5A-5D, which presents DSC traces showing the thermal transitions of polymer films of various compositions. FIG. 5A shows a trace for FECA2.0, the melt of which (trace 301 in the figure) shows evidence for two components, and in which the cooling of the melt (trace 302 in the figure) shows two distinct recrystallizations. The larger peak belongs to the caprolactone segment. FIG. 5B shows DSC traces for dry PECA films of various EO/CL ratios, and FIG. 5C shows DSC traces for wet PECA films of various EO/CL ratios.

Figure 5D:
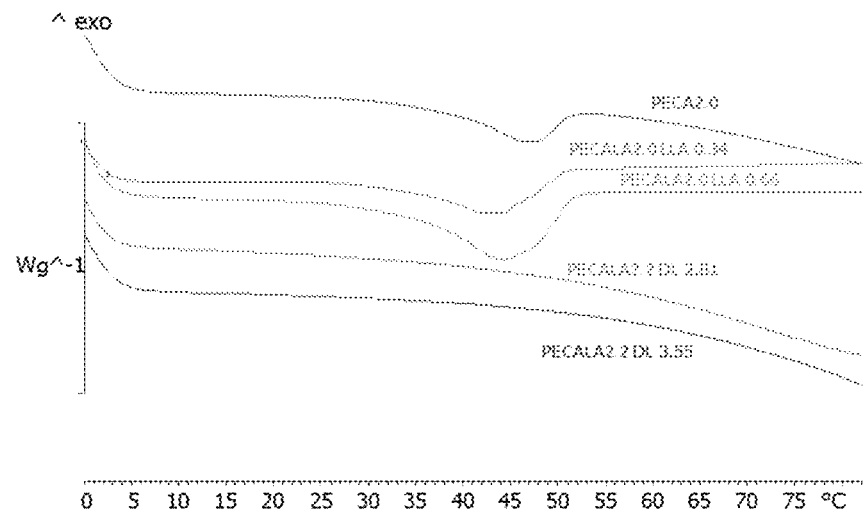

Reference is now made to FIG. 5D, which shows DSC traces for PECALA films of various compositions, with a DSC trace of a PECA2.0 film shown for comparison. These DSC traces support the conjecture that the lactide unit disrupts the crystallinity of the caprolactone segments. The traces show that for PECALA2.2 DL 2.81 and 3.55 films, the incorporation of lactide units destroys the polymer's crystallinity.

Figure 6A:
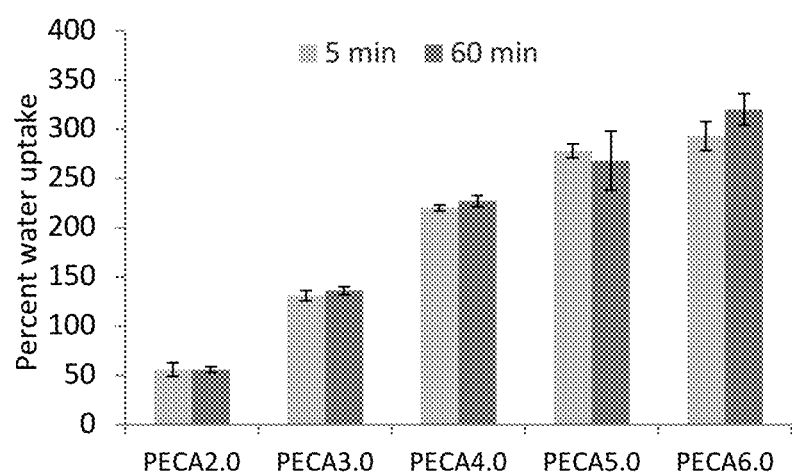
FIGS. 6A-6B presents results of measurements of water uptake by dry PECA films of different ethylene oxide/caprolactone ratios and for dry PECALA films of varying compositions.
Figure 6B:
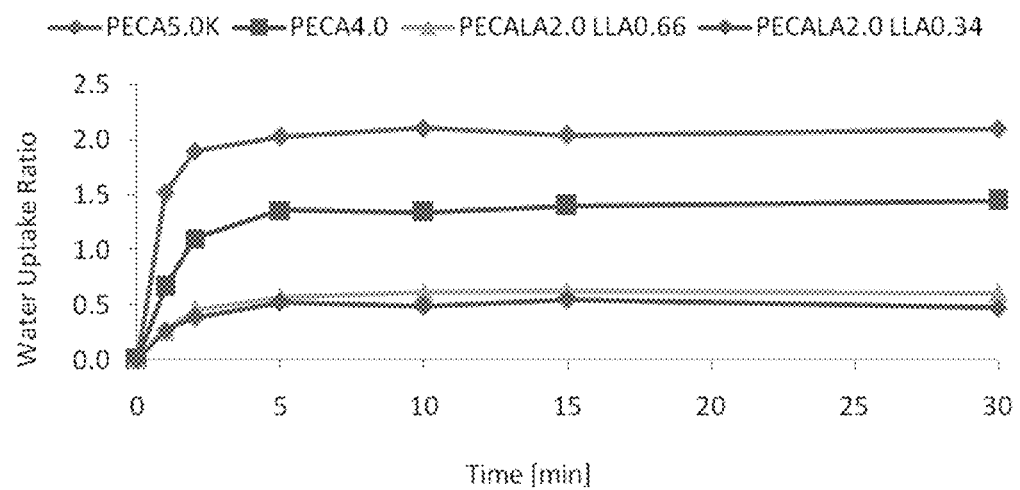

Another important physical property of the polymer films with respect to their use as backings for tissue adhesives is their water uptake. Reference is now made to FIG. 6A, which presents a graph showing results of measurements of the water uptake (w/w, measured gravimetrically) after 5 and 60 minutes of a number of PECA films of various EO/CL ratios. The results show that water rapidly saturates the material. FIG. 6B presents a graph showing results of measurements of the water uptake (w/w, measured gravimetrically) for two PECALA compositions in comparison to two PECA compositions. As with PECA, PECALA saturates rapidly. In preferred embodiments of the invention, the water uptake is 30%-50%, and the half-life for breakdown in water is 15-30 days.

A preferred method of preparing the fibrinogen-based tissue adhesive of the present invention is now disclosed. A non-permeable biocompatible polymer film is cast; in preferred embodiments, the film is made from PECA, PELA, or PECALA. The film can be prepared by any method known in the art. In some preferred embodiments, a solution (typically about 24% w/v) of dry polymer in an organic solvent is prepared, and the solvent then allowed to evaporate. In preferred embodiments of the invention, the solvent is THF, but any sufficiently volatile organic solvent may be used instead. Non-limiting examples of suitable solvents include chloroform, dioxane, acetone, 1-methyl-2-pyrrolidinone, DMF, and DMA. In some preferred embodiments, the solution is covered, e.g. by perforated aluminum foil, so that the solvent does not evaporate too quickly and to prevent dust contamination, which can lead to surface defects.

The film can be of any thickness suitable for the desired final application; in some embodiments, the film has a thickness of approximately 200 μm. In preferred embodiments, the film has a thickness of approximately 100 μm. In typical embodiments of the invention, the polymer film is characterized by a tensile strength of 5-15 MPa, a Young's Modulus (elasticity) of 50-200 MPa; and a melting point of 45-52° C. and/or a softening point of 42-56° C.

The polymer film is then placed on a supporting horizontal surface made of a smooth flat material from which it will be possible to remove the film without damaging it; non-limiting examples of such surfaces include glass and sheets made from inert polymers such as silicone or polytetrafluoroethylene. The film is then softened, in preferred embodiments by heating (typically to about 55-60° C.) or by residual solvent. In preferred embodiments in which the smooth surface is a flexible polymer sheet, a sheet of rigid material such as glass is placed between the polymer sheet and the heating element for ease of handling. The softened film is then covered by a homogeneous fibrin sealant mixture. The mixture typically comprises fibrinogen, thrombin, $CaCl_2$, and optionally additives, as described above. In embodiments of the invention in which the patch is provided as a two-component system, thrombin is not incorporated directly into the polymer, and the fibrin sealant comprises fibrinogen and optionally additives. Non-limiting examples of additives that can be incorporated into the mixture include additives for extending the adhesion half-life such as plasmin inhibitors, pharmaceutically active agents for targeted or sustained release, and analgesics.

The fibrin sealant mixture is then added as a powder to the softened polymer film. The powder may be added by any method known in the art. Non-limiting methods include sprinkling over the polymer film, spraying, spraying a suspension of the powder in a volatile organic solvent onto the film, or simply spreading the powder over the surface of the film. In preferred embodiments, the mixture is added in an amount sufficient to provide 0.5-8 mg of fibrinogen and 20-1000 IU of thrombin/$cm^2$ of film. In embodiments in which the patch is provided as a two-component system, as mentioned above, thrombin is not included in the fibrin sealant, but is applied separately to the affected body part, in preferred embodiments, in concentrations sufficient to provide 20-1000 IU/$cm^2$ of film applied to the body part. The polymer film is then covered with a smooth material having a flat surface; suitable materials described above for the supporting horizontal surface are also suitable for use as the covering surface. In preferred embodiments in which the covering surface is a flexible polymer, the flexible polymer is covered with a rigid smooth material such as a glass plate in order that when the softened film is pressed (see the following paragraph), the pressure on the film is homogeneously applied.

The fibrin sealant mixture is then pressed into the surface of the softened polymer film. The pressing may be done by any method known in the art. In preferred embodiments of the invention, a programmed compression procedure is used in which the compressive force increases during the compression up to a maximum of 50 N. The actual compressive force can be adjusted according to the thickness and composition of the specific film being used; the force need only be sufficient to incorporate the powder into the surface of the softened polymer film. As was discussed above and shown pictorially in FIG. 2, this procedure partially incorporates the sealant into the polymer film, typically to a depth of 20-60 μm, while leaving particles of sealant partially exposed on the surface of the film. Note that in contrast to hemostatic patches and glues known in the art, the hemostatic agent neither remains on the surface of the patch in the form of a free powder, nor is it distributed throughout the polymer backing. Rather, the hemostatic agent is partially incorporated into one surface of the backing and remains in proximity to one surface, while the backing below a depth of about 20-60 μm and the other surface of the backing remain free of hemostatic agent.

After the compression, the film (still between the two smooth flat surfaces) is removed from the heating apparatus and allowed to cool to room temperature at a rate sufficiently slow such that it returns essentially to its original morphology, thus substantially retaining the mechanical, physical, and chemical properties of the film as originally formed. Once the film has returned to room temperature, it may optionally be placed in a freezer (typical freezer temperatures are −15 to −25° C.) for ~15 minutes in order to make it easier to remove the film from the surfaces between which it sits. In embodiments in which the horizontal supporting surface and upper covering surface are made of a flexible material, freezing is generally not necessary, since the film can be peeled from the backing surfaces without risk of damage.

Excess powder, if any, is removed (e.g. by shaking or gently blowing) from the film and the film removed from the flat surface on which it was prepared. It is emphasized that in contrast to hemostatic patches known in the art, in preferred embodiments of the invention herein disclosed, no hemostatic agent remains on the surface of the patch in the form of a free powder; any agent that the procedure described above fails to incorporate into the backing is discarded. The resulting patch is ready for use and can be applied directly to tissue. The films are stable to long-term storage in a dry environment at temperatures of 2-25° C. Long-term storage is typically performed by placing the film in a sealed plastic envelope in a dry refrigerated environment, typically at a temperature of 4-8° C.

The invention herein disclosed is now illustrated by the following non-limiting examples that are provided to aid one of ordinary skill in the art to make and use the invention as claimed.

Example 1

A 4.3% w/v solution of dry PECALA in THF was prepared and poured into a glass Petri dish. The dish was covered with perforated aluminum foil and left overnight at room temperature in a fume hood. The resulting film had a thickness of approximately 200 μm.

Figure 7:
FIG. 7 shows a photograph of a fibrinogen-based tissue adhesive film according to one embodiment of the present invention.

2 cm squares of the film were excised and placed on a glass slide. The samples were then placed on a 58° C. hotplate until the polymer was softened. A powdered fibrin sealant mixture containing fibrinogen, thrombin, and $CaCl_2$ was sprinkled onto the surface of the softened polymer film, and the film covered with a second glass slide. The fibrin sealant mixture was then pressed into the surface of the softened polymer film by using an Instron Universal Testing Machine programmed to apply an increasing compressive force to a maximum of 50 N. Following the compression, the glass slide was slowly cooled to room temperature. The slide was then placed in a freezer at −22° C. for 15 minutes in order to help loosen the film from the slide. Excess powder was removed from the surface by shaking, and the patch removed from the glass slide using a surgical scalpel. Reference is made to FIG. 7, which shows a photograph of the patch thus obtained, which is ready for use.

Example 2

Figure 8:
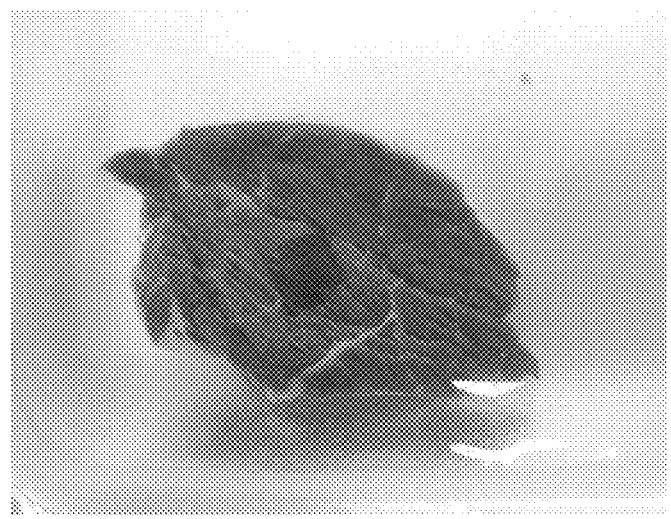
FIG. 8 shows a photograph of fibrinogen-based tissue adhesive film according to one embodiment of the present invention attached to a piece of raw meat after 60 minutes of washing under running water.

An adhesive tissue patch according to one embodiment of the present invention was prepared and attached to a piece of raw meat and then washed extensively under a stream of water. As shown in FIG. 8, the patch remained firmly attached even after 60 minutes of washing.

Example 3

Figure 9:
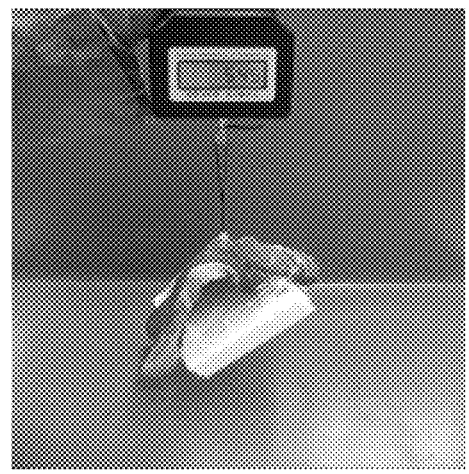
FIG. 9 shows a photograph of a typical measurement of the force required to detach the adhesive film of the present invention from raw meat used as a substrate.

Measurements were made of the adherence of an adhesive tissue patch disclosed in the present invention. A patch was prepared and applied to a piece of raw meat by manually pressing for 2 minutes. A tension and compression force gauge was used to measure the force needed to detach a 2 cm×2 cm patch. Reference is now made to FIG. 9, which shows a photograph of a typical force measurement. It was found that a force of 5-7 Newton is required to detach the film.

Example 4

In-vivo biodegradability assessments were made following intraperitoneal (IP) implantation of adhesive patches of the present invention onto liver and intestinal (cecum) surfaces of rats. The implantations had no visible effect on the animals, which appeared healthy and gained weight during the fourteen days following the implantation.

Fourteen days after implantation of the patches, the animal was sacrificed and a gross necropsy performed, during which the abdominal cavity was opened and a macroscopic assessment of the status of the patch made. The patches could be detected attached to the implantation targets.

Figure 10A:
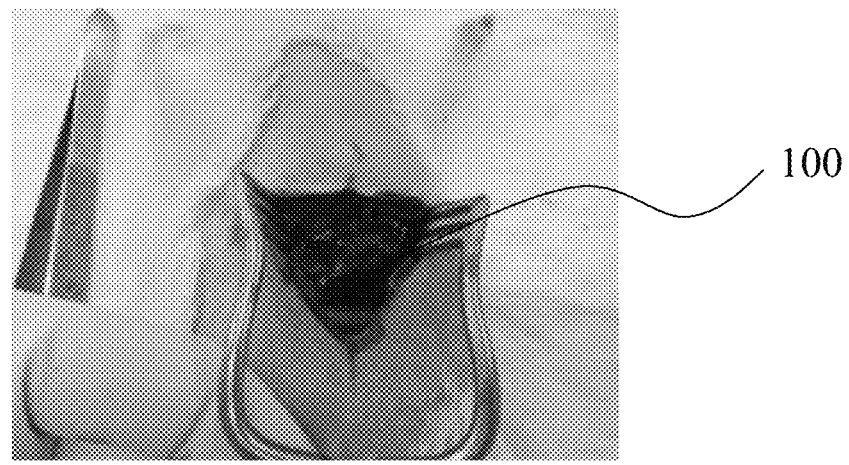
FIGS. 10A-10D shows photographs illustrating an in-vivo biodegradability assessment and adhesion/detachment force measurement.
Figure 10B:
Figure 10C:
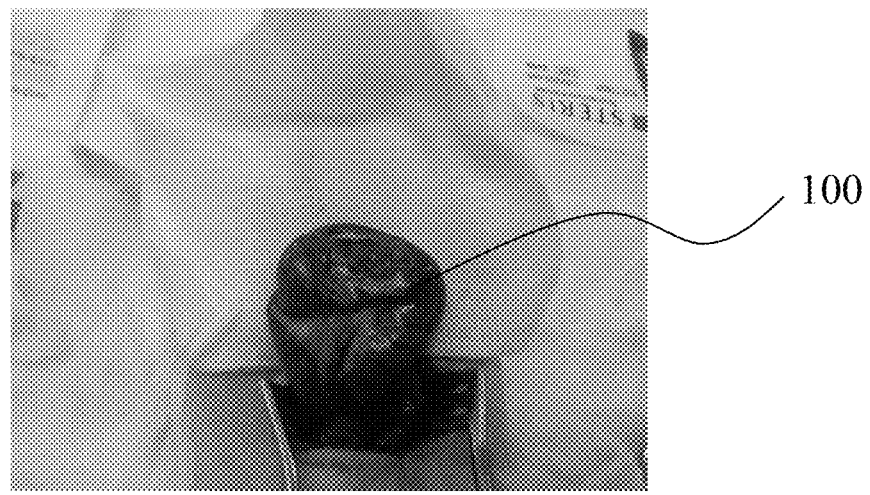
Figure 10D:
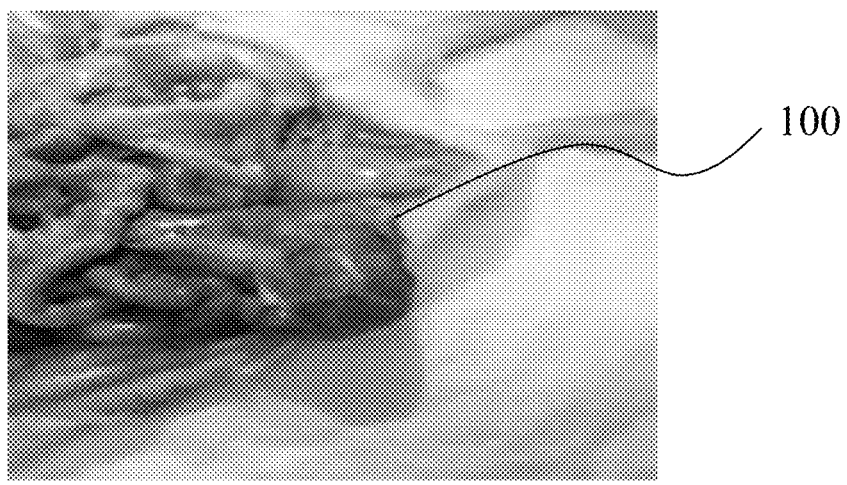

Reference is now made to FIG. 10A, which shows the implantation site for implantation of adhesive patch 100 on the liver at day 0, and to FIG. 10B, which shows the implantation site for implantation of adhesive patch 100 on the liver on day 14 following the implantation. FIGS. 10C and 10D show the implantation site for implantation on the caecum at days 0 and 14, respectively.

As can be seen from the figures, the adhesive patches remained visibly attached to the implantation site 14 days after implantation.

Example 5

A patch was prepared as described in Example 1 above, except that instead of a sealant mixture containing fibrinogen, thrombin, and $CaCl_2$, only powdered fibrinogen was sprinkled onto the surface of the softened polymer film. A solution of thrombin was sprayed onto a piece of raw meat and the patch pressed onto the meat for 2 minutes. The adherence of the patch prepared in this manner was identical to that of that of a patch applied as described in Example 3.

Example 6

Figure 11:
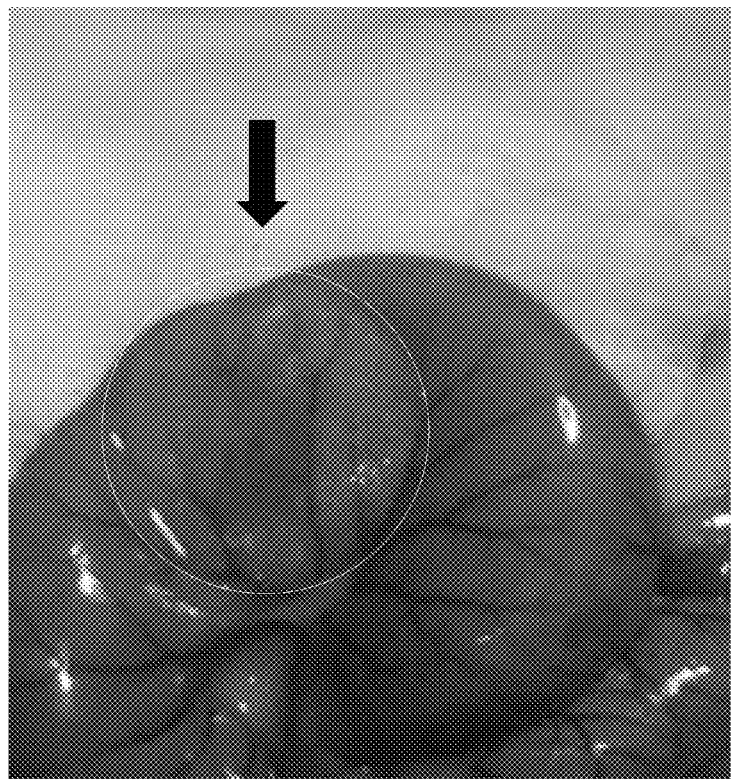
FIG. 11 shows the use of an adhesive patch of the present invention to seal a 3 mm hole in a rat caecum; and, FIG. 12 shows the use of an adhesive patch of the present invention to seal a 5 mm puncture hole in a rat liver.

An in vivo study was performed to demonstrate the efficacy of the patch of the present invention in sealing damaged tissue. Rats (n=6) were used as the test animals. A 2-3 mm hole was made in the caecum of each of tested animal using a biopsy punch. In the experimental group (n=3), the hole was then covered with a 1.4 cm diameter patch of the present invention made of PECALA and containing 2 mg/cm² fibrin sealant. Reference is now made to FIG. 11, which shows the area of the caecum that had been punctured and then covered with the patch of the present invention (circle and arrow indicating the region). The caecum of animals in the control group (n=3) was punctured, but no further treatment was performed. After the puncture was made (and sealed with the patch in the case of the test group), the caecum was returned to the abdominal cavity. The animals were followed for two weeks following the operation and then sacrificed.

All of the animals in the experimental group gained weight and showed no side effects. Necropsy data showed that the caecum of the treated animals had healed completely, the patch was absorbed into the tissue, and no local reaction could be detected. In contrast, two of the three control (untreated) animals died after experiencing severe inflammation of the abdomen.

The results of this study demonstrate that the patch of the present invention is effective in sealing intestinal leakage in a rat caecum model.

Example 7

Figure 12:
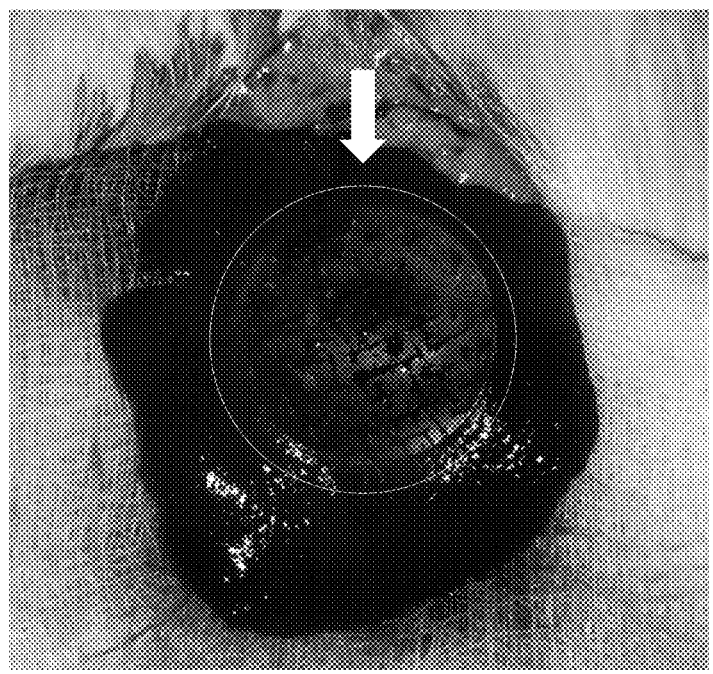

A second in vivo study was performed to demonstrate the efficacy of the patch of the present invention in stopping severe bleeding. Rats (n=6) were used as the test animals. In this study, a 6 mm hole was made in the left lobe of the liver of the test animals using a biopsy punch, resulting in severe bleeding. The hole was then covered with a 1.4 cm diameter patch of the present invention made from PECALA and containing 2 mg/cm$^2$ fibrin sealant. The device adhered well to the tissue, sealing the hole and stopping the bleeding instantly. Reference is now made to FIG. 12, which shows the liver of an experimental animal after the puncture and application of the patch (the puncture hole can be seen beneath the transparent patch). After hemostasis was evident, the liver was returned to the abdominal cavity. The animals were kept alive for two weeks following the treatment and then sacrificed.

All of the experimental animals gained weight and showed normal behavior with no side effects. Necropsy data showed that the liver completely recovered and that the patch had been degraded and absorbed with no reaction at the site of the injury.

These results demonstrate that the patch of the current invention is effective for stopping severe bleeding with no side effects.

We claim:

1. A fibrinogen-based tissue adhesive patch, comprising:
a backing comprising a film made of a biocompatible polymer; and
a fibrinogen sealant;
wherein:
said backing is characterized by a thickness of about 100-200 μm, and said backing does not comprise an interpenetrating network;
said fibrinogen sealant is incorporated into at least one surface of said biocompatible polymer backing to a depth of between 20 microns and 60 microns by physically pressing said fibrinogen sealant into said at least one surface such that said fibrinogen sealant remains partially exposed on said at least one surface; and
said tissue adhesive patch does not include any mesh or woven component.

2. The tissue adhesive patch according to claim 1, wherein said backing comprises a film made of a biocompatible polyurethane polymer comprising units of a biocompatible polymer connected by isocyanate linkages.

3. The tissue adhesive patch according to claim 2, wherein said biocompatible polymer is selected from the group consisting of polyethylene glycol-polycaprolactone copolymers; polyethylene glycol-DL-lactide copolymers; and polyethylene glycol-polycaprolactone-DL-lactide copolymers.

4. The tissue adhesive patch according to claim 2, wherein said polyurethane linkages are the product of reaction between two biocompatible polymer units and hexamethylene diisocyanate.

5. The tissue adhesive patch according to claim 1, wherein said backing is characterized by at least one physical characteristic selected from the group consisting of:
a Young's Modulus of between 50 MPa and 200 MPa;
a tensile strength of between 5 MPa and 15 MPa;
a melting point of between 45° C. and 52° C.;
a water uptake of between 30% and 50%; and,
a half-life for breakdown in water of between 15 days and 30 days.

6. The tissue adhesive patch according to claim 1, wherein said backing is characterized by a thickness of about 100 μm.

7. The tissue adhesive patch according to claim 1, wherein said patch is configured such that contact between said adhesive patch, a tissue, and a fluid, activates said fibrinogen sealant such that said fibrinogen sealant acts to attach said backing to said tissue.

8. The tissue adhesive patch according to claim 1, wherein said fibrinogen sealant is not distributed throughout said backing.

9. The tissue adhesive patch according to claim 1, wherein said fibrinogen sealant comprises fibrinogen, thrombin, and $CaCl_2$).

10. The tissue adhesive patch according to claim 1, wherein said fibrinogen sealant comprises fibrinogen but does not comprise thrombin.

11. The tissue adhesive patch according to claim 1, wherein said tissue adhesive patch does not comprise any hemostatic agent in the form of a free powder.

12. The tissue adhesive patch according to claim 1, wherein said fibrinogen sealant additionally comprises at least one additive.

13. The tissue adhesive patch according to claim 12, wherein said additive is selected from the group consisting of additives for extending the adhesion half-life of said film, pharmaceutically active agents, and analgesics.

14. A method for producing a fibrinogen-based tissue adhesive patch, wherein said method comprises:
casting a polymer film made from a biocompatible polymer, wherein said polymer film is characterized by a thickness of about 100-200 μm;
softening said polymer film;
placing a fibrinogen sealant on at least one surface of said polymer film; and
pressing said polymer film until at least a portion of said fibrinogen sealant is incorporated into said at least one surface of said polymer film to a depth of between 20 microns and 60 microns.

15. The method according to claim 14, wherein said step of casting a polymer film comprises casting a polymer film from a biocompatible crosslinked polyurethane polymer comprising units of a biocompatible block copolymer connected by polyurethane linkages, said biocompatible block copolymer selected from the group consisting of polyethylene glycol-polycaprolactone copolymers; polyethylene glycol-DL-lactide copolymers; and polyethylene glycol-polycaprolactone-DL-lactide copolymers.

16. The method according to claim 14, wherein said step of placing a fibrinogen sealant on at least one surface of said polymer film comprises placing on at least one surface of said polymer film a fibrinogen sealant selected from the group consisting of:

fibrinogen sealants comprising fibrinogen, thrombin, and $CaCl_2$); and, fibrinogen sealants comprising fibrinogen but not comprising thrombin.

17. The method according to claim 14, wherein said step of casting a polymer film comprises:

preparing a solution of a dry polymer in an organic solvent; and, evaporating said organic solvent.

18. The method according to claim 14, wherein said step of casting a polymer film comprises casting said polymer film on a surface made of a material selected from the group consisting of glass, silicone, and polytetrafluoroethylene.

19. The method according to claim 18, wherein said step of casting a polymer film comprises casting said polymer film on a silicone sheet placed on a hard surface.

20. The method according to claim 18, further comprising a step of removing said polymer film from said surface following said step of pressing said polymer film.

21. The method according to claim 20, further comprising a step of placing said polymer film in a freezer following said step of pressing said polymer and prior to said step of removing said polymer film from said surface.

22. The method according to claim 14, wherein said step of softening said polymer film comprises softening said polymer film by a method selected from the group consisting of heating said polymer film until said polymer film softens and softening said polymer film by using residual solvent.

23. A method of treating a leak of fluid into or out of a body part, comprising applying a tissue adhesive patch according to claim 1 to said body part such that contact with said fluid activates said fibrinogen sealant whereby said activated fibrinogen sealant attaches said polymer backing to said body part, thereby sealing said body part.

24. The method according to claim 23, wherein said leak of fluid is selected from the group consisting of arterial bleeding; organ tissue bleeding; bile anastomosis; cerebrospinal fluid leak; dura leak; and air leak in damaged lung tissue.

25. A method of treating a leak of fluid into or out of a body part, comprising applying a tissue adhesive patch produced according to the method of claim 14 to said body part such that contact with said fluid activates said fibrinogen sealant whereby said activated fibrinogen sealant attaches said polymer backing to said body part, thereby sealing said body part.

26. The method according to claim 25, wherein said leak of fluid is selected from the group consisting of arterial bleeding; organ tissue bleeding; bile anastomosis; cerebrospinal fluid leak; dura leak; and air leak in damaged lung tissue.

27. The tissue adhesive patch according to claim 2, wherein said biocompatible polymer is a polyethylene glycol-polycaprolactone-DL-lactide copolymer.

28. The tissue adhesive patch according to claim 27, wherein said polyurethane linkages are the product of reaction between two biocompatible polymer units and hexamethylene diisocyanate.

* * * * *